(12) United States Patent
Sejergaard et al.

(10) Patent No.: US 10,851,364 B2
(45) Date of Patent: Dec. 1, 2020

(54) METHOD OF CONTROLLING A POLYPEPTIDE MODIFICATION REACTION

(71) Applicant: Novo Nordisk Healthcare AG, Zurich (CH)

(72) Inventors: Lars Sejergaard, Albertslund (DK); Janus Krarup, Gentofte (DK)

(73) Assignee: NOVO NORDISK HEALTHCARE AG, Zurich (CH)

( * ) Notice: Subject to any disclaimer, the term of this patent is extended or adjusted under 35 U.S.C. 154(b) by 0 days.

(21) Appl. No.: 15/919,688

(22) Filed: Mar. 13, 2018

(65) Prior Publication Data

US 2018/0362953 A1 Dec. 20, 2018

Related U.S. Application Data

(63) Continuation of application No. 14/934,199, filed on Nov. 6, 2015, now abandoned, which is a continuation of application No. 12/994,409, filed as application No. PCT/EP2009/056675 on May 29, 2009, now abandoned.

(60) Provisional application No. 61/059,129, filed on Jun. 5, 2008.

(30) Foreign Application Priority Data

May 30, 2008 (EP) .................... 08157300

(51) Int. Cl.
| | |
|---|---|
| *C07K 14/745* | (2006.01) |
| *C12N 9/64* | (2006.01) |
| *G01N 33/86* | (2006.01) |

(52) U.S. Cl.
CPC .......... *C12N 9/6437* (2013.01); *G01N 33/86* (2013.01); *C12Y 304/21021* (2013.01)

(58) Field of Classification Search
None
See application file for complete search history.

(56) References Cited

U.S. PATENT DOCUMENTS

| | | | |
|---|---|---|---|
| 4,286,056 | A | 8/1981 | Andary et al. |
| 4,456,591 | A | 6/1984 | Thomas |
| 2007/0197440 | A1 | 8/2007 | Grancha Gamon et al. |

FOREIGN PATENT DOCUMENTS

| | | |
|---|---|---|
| CN | 1630721 A | 6/2005 |
| EP | 1820509 A1 | 8/2007 |
| JP | H08-237145 A | 9/1996 |
| JP | 2007-217415 A | 8/2007 |
| WO | 99/66031 A2 | 12/1999 |
| WO | 02/22776 A2 | 3/2002 |
| WO | 2007/013993 A1 | 2/2007 |

OTHER PUBLICATIONS

Bjorn et al., Research Disclosure, 1986, vol. 9, p. 26960.
Bladbjerg et al., Scandinavian Journal of Clinical and Laboratory Investigations, 1994, vol. 54, No. 7, p. 505-514.
Bom et al, Biochemical Journal, 1990, vol. 265, No. 2, p. 327-336.
Griffin, Proceedsing of the National Academy of Sciences of the USA, 1978, vol. 75, No. 4, p. 1998-2002.
Krarup et al., Abstracts of Papers—American Chemical Society, 2003, Voil. 225, No. 1-2, BIOT333.
Mollerup et al., Biotechnology and Bioengineering, 1995, vol. 48, No. 5, p. 501-505.
Nakashima et al., Humana Press, 2005, p. 177.
Neuenschwander et al., Journal of Biological Chemistry, 1993, vol. 268, No. 29, p. 21489-21492.
Pedersen et al., Biochemistry, 1989, vol. 28, p. 9331-9336.
Walsh et al., Journal of Clinical Investigation, 1984, vol. 73, No. 5, p. 1392-1399.

*Primary Examiner* — Marsha Tsay
(74) *Attorney, Agent, or Firm* — Jianjie Hu

(57) ABSTRACT

The invention relates to a method of controlling a polypeptide modification reaction, in particular but not exclusively, a method of controlling the activation of human factor VII (FVII) to produce human factor VII(a) (FVII(a)). The invention also relates to polypeptides obtainable by the polypeptide modification reaction and to pharmaceutical compositions comprising said polypeptides.

13 Claims, 5 Drawing Sheets

METHOD OF CONTROLLING A POLYPEPTIDE MODIFICATION REACTION

CROSS-REFERENCE TO RELATED APPLICATIONS

This application is a continuation of U.S. application Ser. No. 14/934,199, filed Nov. 6, 2015, which is a continuation of U.S. application Ser. No. 12/994,409, filed Mar. 10, 2011 (now abandoned), which is a 35 U.S.C. § 371 national stage application of International Patent Application PCT/EP2009/056675 (published as WO 2009/144318 A1), filed May 29, 2009, which claimed priority of European Patent Application 08157300.8, filed May 30, 2008; this application further claims priority under 35 U.S.C. § 119 of U.S. Provisional Application 61/059,129, filed Jun. 5, 2008; the contents of which are incorporated herein by reference.

FIELD OF THE INVENTION

The invention relates to a method of controlling a polypeptide modification reaction, in particular but not exclusively, a method of controlling the activation of human factor VII (FVII) to produce human factor VII(a) (FVII(a)). The invention also relates to polypeptides obtainable by the polypeptide modification reaction and to pharmaceutical compositions comprising said polypeptides.

BACKGROUND OF THE INVENTION

Blood coagulation is a process consisting of a complex interaction of various blood components (or factors) that eventually gives rise to a fibrin clot. Generally, the blood components, which participate in what has been referred to as the coagulation "cascade", are enzymatically inactive proteins (proenzymes or zymogens) that are converted to proteolytic enzymes by the action of an activator (which itself is an activated clotting factor). Coagulation factors that have undergone such a conversion are generally referred to as "active factors", and are designated by the addition of the letter "a" to the name of the coagulation factor (e.g. Factor VIIa)).

FVII (also known as Single chain FVII, unactivated FVII or zymogen) is a single polypeptide chain, which upon proteolytic cleavage of the peptide bond between Arg152 and Ile153 is converted into the activated form: FVII(a). This reaction can be catalyzed by FVII(a) auto-proteolysis or by other enzymes such as FXa or Russel viper venom. Auto activation has the advantage that no enzyme needs to be added and physically removed at the end of the process.

It is very important to be able to control the activation of FVII carefully, as the content of heavy chain degradation products (AA290 and AA315) increases dramatically once a proportion of activation of more than 99% is reached (i.e. once the preferred substrate of Arg 152 has become depleted). It is therefore crucial not to over-activate the product. A high proportion of activation e.g. above 94% is at the same time desirable, leaving a rather narrow interval (e.g. 94-99%) where both a low degradation content and high activity can be obtained.

A certain amount of enzyme activation will take place concurrently during purification of the enzyme. Furthermore, the levels of activation during the purification process will inevitably vary due to variations in starting material composition—mainly FVII(a) titer and hence column load. Unexpected holding time during purification will also give rise to variations in the levels of activation. During purification, the FVII(a) molecules will experience varying conditions with respect to concentration, pH, temperature and residence time, which will result in partial activation. Following purification, it has been observed that the proportion of activation has varied widely (e.g. 16% to 74%) depending upon the purification technique and conditions. This variation in the proportion of activation following purification creates a significant problem with respect to conducting a standardised activation process following purification.

The proportion of activation of FVII can be calculated through known procedures, however, no real-time measurement technique currently exists and the known procedures typically have a duration of approximately 30 minutes. Therefore, if the proportion of activation is approaching 99% upon sample removal for measurement, then this value will be exceeded by the time the results are obtained. This will result in high levels of the undesirable heavy chain degradation products.

U.S. Pat. No. 4,286,056 (Baxter Travenol Lab) describes a method for producing activated prothrombin complex concentrate which comprises controlling the degree of activation by determining the activation state of the starting material and then varying at least one of the activation conditions in accordance with analyses of the progress of activation of the starting material to arrive at a predetermined activation level. WO 2007/013993 (Maxygen Holdings Ltd) describes a method for activating FVII to FVII(a) in solution, comprising addition of an amine compound, $Ca^{2+}$, adjusting the final pH of the solution to about 7.2 to 8.6, incubating the resulting activation mixture at between about 2° C. and about 25° C. for an amount of time sufficient to convert at least 90% of the scFVII to FVII(a). U.S. Pat. No. 4,456,591 (Baxter Travenol Lab) describes a process of administering to a patient having a clotting factor defect such as a deficiency or inhibitor an effective hemostatic amount of a composition in which the sole effective, activated hemostatic agent is factor VII(a).

There is thus a great need for providing an improved method for determining the optimum reaction time to provide desired levels of modified enzyme.

The current invention also provides for a purer protease product. A purer product is less likely to result in antiprotease (antibody) formation in the patient.

Furthermore, tight control of the rate of protease activation ultimately results in reduced waste in a production plant, as fewer production batches will be discarded when a greater number of batches meets the specified requirements, in terms of purity and evenness of quality.

SUMMARY OF THE INVENTION

According to a first aspect of the invention there is provided a method of controlling a polypeptide modification reaction which comprises the steps of calculating at least one process variable and applying said variable to a mathematical model in order to calculate the value of a further process variable.

According to a second aspect of the invention there is provided a method of performing a polypeptide modification reaction which comprises the steps of:
(a) measuring the initial concentration of the polypeptide;
(b) measuring the initial proportion of modified polypeptide;
(c) calculating the polypeptide modification reaction time by correlation of the values calculated in each of steps (a) and (b) with a value of required proportion of modified polypeptide; and (d) performing the polypeptide modification reaction for the time calculated in step (c).

According to a third aspect of the invention there is provided a polypeptide obtainable according to the method as defined hereinbefore.

DRAWINGS

Figure 1:
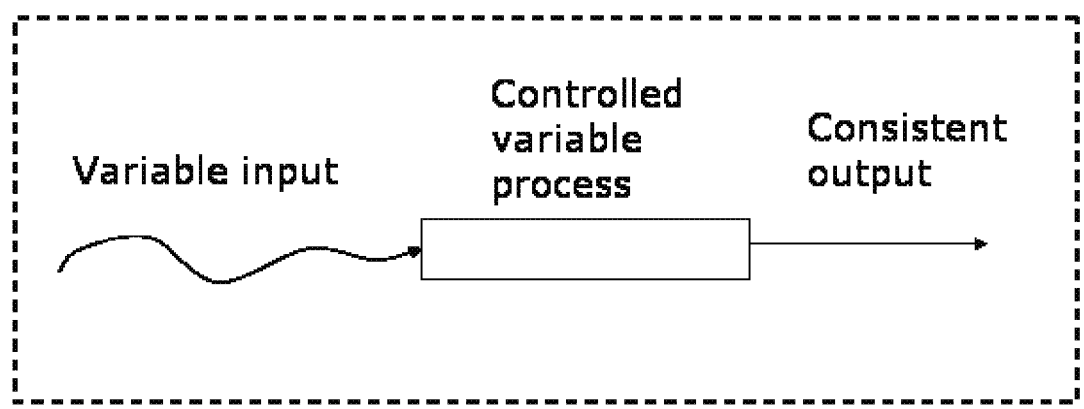
FIG. 1 illustrates the overall concept of the invention. With varied input, the process ensures that the output is essentially predictable and constant.
Figure 2:
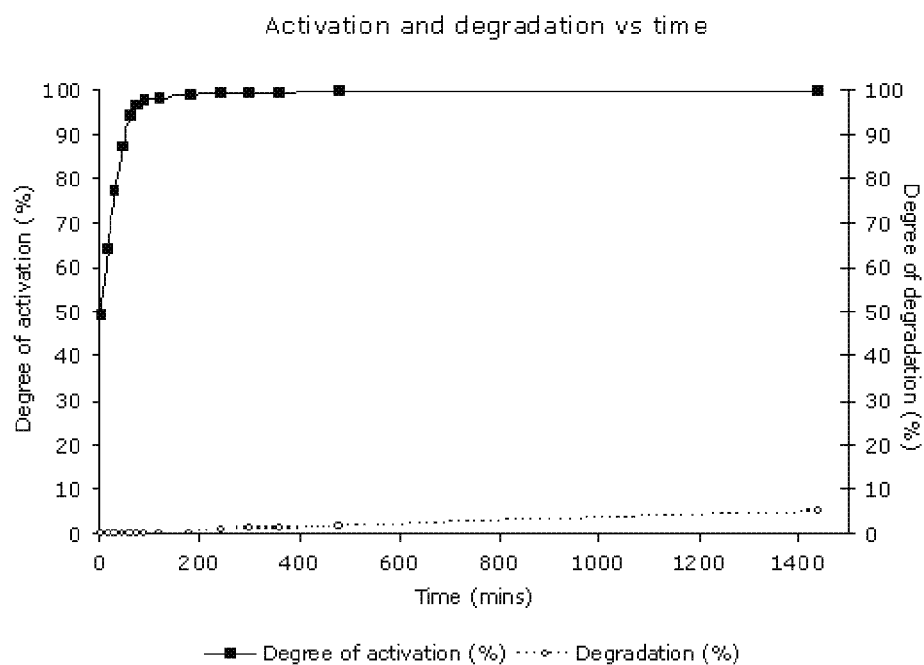
FIG. 2 illustrates the importance of closely regulating the degree to which a protease is activated. As the degree of activation (%) increases from 99.5% towards 100%, the percentage of degraded product (protease) increases exponentially.
Figure 2:
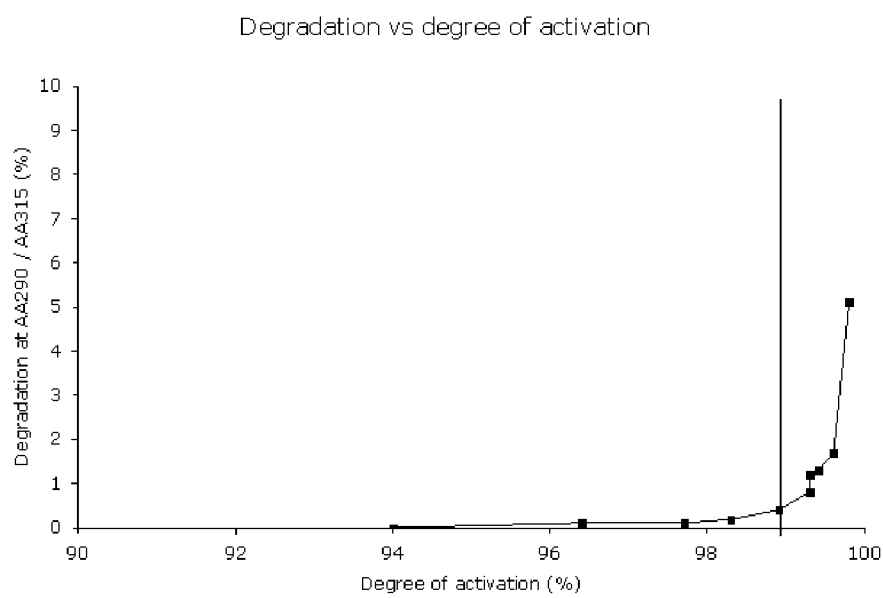
Figure 3:
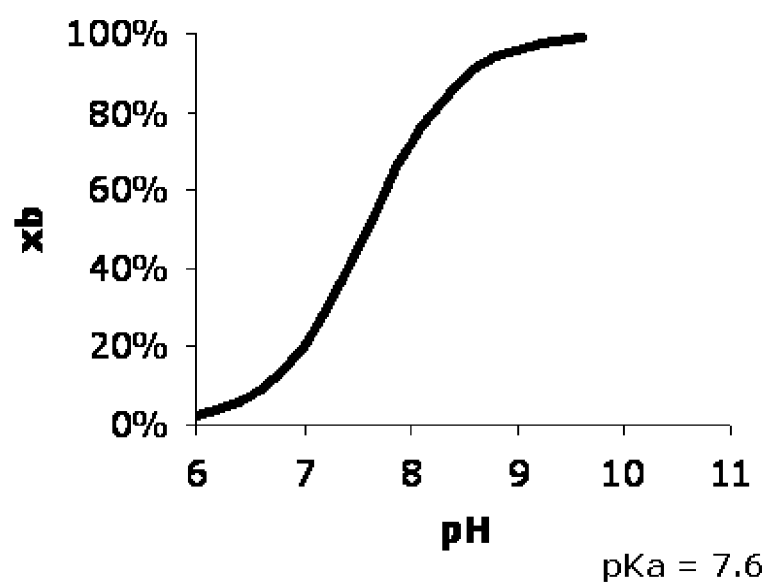

FIG. 3 illustrates that the more enzyme (that is, protease) present in a batch, the faster activation of a protease will occur. The molar fraction (xb) stated as a percentage can be found using the Henderson-Hasselbach diagram. The active fraction of the enzyme can be calculated for any pH. There is nonlinear correlation.

Figure 4:
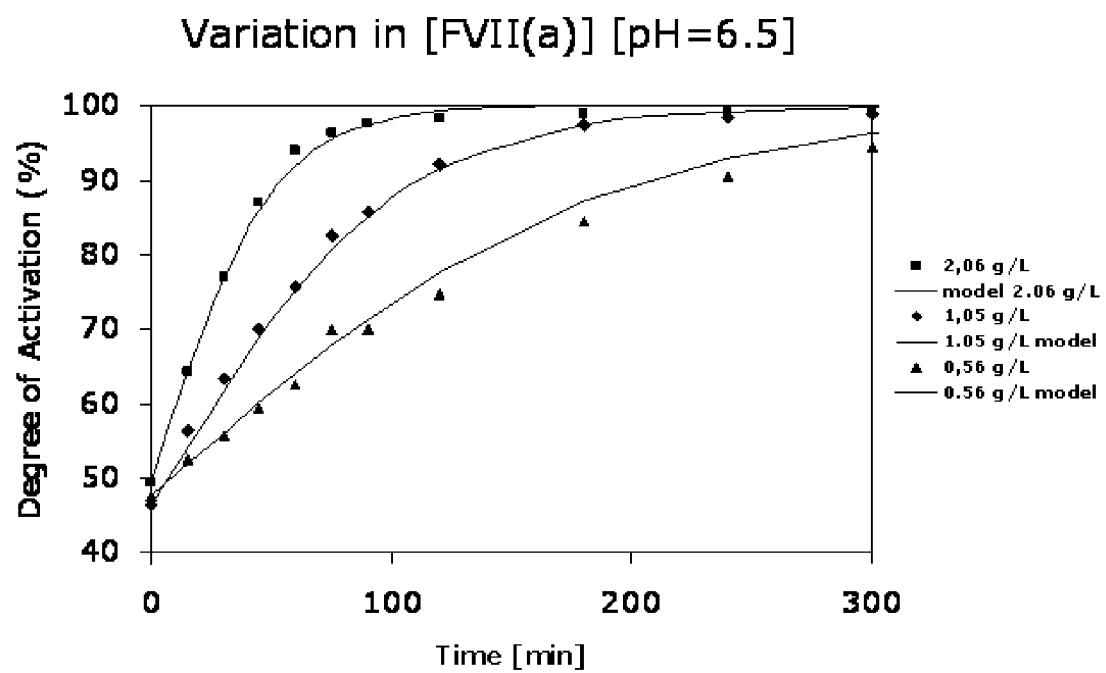

FIG. 4 shows that the concentration of FVII(a) obtained is concentration dependent. At high FVII(a) concentration, the rate of FVII activation is greater than at low FVII(a) concentration.

Figure 5:
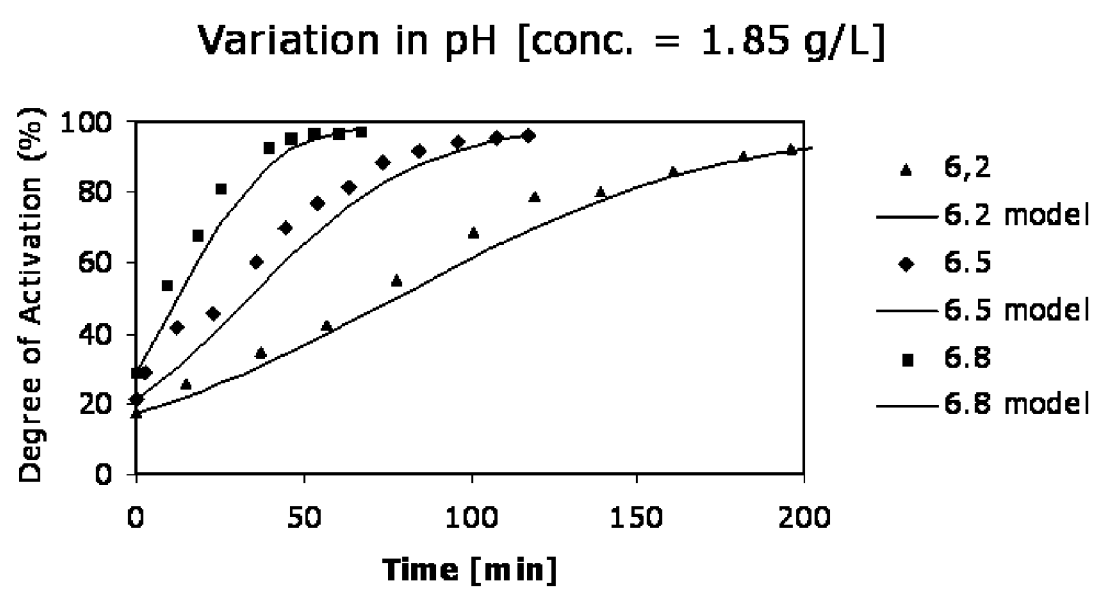

FIG. 5 shows that the concentration of FVII(a) obtained is pH-dependent. At a higher pH (6.8) the rate of FVII activation is higher; at a lower pH (6.2), the rate of FVII activation is lower and at pH 6.5 the rate of FVII activation is intermediate.

DETAILED DESCRIPTION OF THE INVENTION

According to a first aspect of the invention there is provided a method of controlling a polypeptide modification reaction which comprises the steps of calculating at least one process variable and applying said variable to a mathematical model in order to calculate the value of a further process variable.

The invention therefore provides the benefit of combining a physical or mathematical model with a process analytical technology (PAT) tool in order to evaluate an essential process variable. The PAT tool has the advantage of being applied in an on-line, in-line and/or at-line manner to accurately control the modification reaction. Thus, the use of such a technique provides the user with an immediate required value such that the reaction can be performed in an optimum manner to achieve optimum results. In one embodiment, the at least one process variable may be selected from degree of modification, reagent concentration measurements, pH measurements, temperature measurements. In one embodiment, the further process variable may be reaction time.

In one embodiment, the method comprises controlling the degree of pegylation of a polypeptide. Thus according to a further aspect of the invention there is provided a method of controlling the degree of pegylation of a polypeptide which comprises the steps of applying the degree of required pegylation, enzyme concentration, PEG concentration, polypeptide concentration and temperature to a mathematical model and calculating the reaction time.

In one embodiment, the method comprises controlling the degree of pegylation of a factor IX (FIX) polypeptide. In one embodiment, the degree of pegylation is calculated in accordance with the following process variables: reaction time, enzyme concentration, PEG concentration, FIX concentration and temperature (which will typically be 22° C.). It will be appreciated that the skilled person will be able to calculate the optimum reaction time to achieve a required degree of pegylation of FIX by inputting values of the process variables into a mathematical model (which may be derived from the Eulers, Runge-Kutta, Newton-Raphson or DASPK methods). Such mathematical methods can be advantageously employed to provide accurate control of polypeptide modification reactions.

According to a second aspect of the invention there is provided a method of performing a polypeptide modification reaction which comprises the steps of:
(a) measuring the initial concentration of the polypeptide;
(b) measuring the initial proportion of modified polypeptide;
(c) calculating the polypeptide modification reaction time by correlation of the values calculated in each of steps (a) and (b) with a value of required proportion of modified polypeptide; and
(d) performing the polypeptide modification reaction for the time calculated in step (c).

In one embodiment, the modification reaction comprises enzymatic cleavage or modification by the addition of a chemical agent to a polypeptide (e.g. pegylation).

In the embodiment wherein modification comprises enzymatic cleavage, it has been surprisingly found that the initial concentration and proportion of cleavage can be correlated with the required proportion of cleavage in order to calculate a precise reaction time. The results of this correlation are extremely accurate (often to within approximately 0.5% proportion of cleavage) and repeatable. The process also provides the significant advantage that only two measurements need to be calculated prior to reaction (namely initial concentration and proportion of cleavage). Furthermore, the reaction may proceed for the calculated time without the need for monitoring the state of the reaction (or even measuring the final proportion of cleavage, unless required for quality control purposes).

The term "protein", "polypeptide" and "peptide" as used herein means a compound composed of at least five constituent amino acids connected by peptide bonds. The constituent amino acids may be from the group of the amino acids encoded by the genetic code and they may be natural amino acids which are not encoded by the genetic code, as well as synthetic amino acids. Natural amino acids which are not encoded by the genetic code are e.g. hydroxyproline, γ-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), Tle (tert-butylglycine), β-alanine, 3-aminomethyl benzoic acid and anthranilic acid.

In one embodiment, the polypeptide is an enzyme, such as a blood coagulation factor or hemostasis related related protein. (e.g. a serine protease). Examples of such polypeptides include: I (fibrinogen), II (prothrombin), tissue factor, V (proaccelerin), VI, VII, VIII, IX (Christmas factor), X (Stuart-Prower factor), XI (plasma thromboplastin antecedent), XII (Hageman factor), XIII (fibrin-stabilizing factor), von Willebrand factor, prekallikrein, high molecular weight kininogen (HMWK), fibronectin, antithrombin III, heparin cofactor II, protein C, protein S, protein Z, protein Z-related protease inhibitor (ZPI), plasminogen, alpha 2-antiplasmin, tissue plasminogen activator (tPA), urokinase, plasminogen activator inhibitor-1 (PAI1), plasminogen activator inhibitor-2 (PAI2) and cancer procoagulant.

In a further embodiment, the polypeptide is an autoactivated polypeptide. In a further embodiment, the enzyme is a blood coagulation factor (e.g. a serine protease blood coagulation factor). Examples of suitable serine protease blood coagulation factors include those classified under EC 3.4.21, for example: II, VII, IX, X, XI, XII, prekallikrein, protein C and plasminogen (the activated forms of these inactive zymogens are FIIa, FVIIa, FIXa, FXa, FXIa, FXIIa, kallikrein, activated protein C (aPC) and plasmin, respectively).

In one embodiment wherein the modification reaction comprises enzymatic cleavage, the blood coagulation factor is factor VII or an analogue or derivative thereof.

In one embodiment wherein the modification reaction comprises pegylation, the blood coagulation factor is factor IX or an analogue or derivative thereof.

In one aspect of the invention, the invention provides a method of activating a serine protease blood coagulation factor which comprises the steps of:
(a) measuring the initial concentration of the serine protease blood coagulation factor;
(b) measuring the initial proportion of activated serine protease blood coagulation factor;
(c) calculating the serine protease blood coagulation factor activation reaction time by correlation of the values measured in each of steps (a) and (b) with a value of required proportion of activated serine protease blood coagulation factor; and
(d) performing the serine protease blood coagulation factor activation reaction for the time calculated in step (c);
(e) terminating the reaction after the reaction time calculated in step (c).

According to a further aspect, the invention provides a method of activating factor VII to factor VII(a), or an analogue or derivative thereof, which comprises the steps of:
(a) measuring the initial concentration of factor VII;
(b) measuring the initial proportion of activated factor VII;
(c) calculating the factor VII activation reaction time by correlation of the values calculated in each of steps (a) and (b) with a value of required proportion of activated factor VII; and
(d) performing the factor VII activation reaction for the time calculated in step (c).

In a further optional step (e), the reaction is terminated after the reaction time calculated in step (c).

In a still further aspect, the invention provides a method of preventing degradation of an activated serine protease product which comprises the steps of:
(a) measuring the initial concentration of the serine protease blood coagulation factor;
(b) measuring the initial proportion of activated serine protease blood coagulation factor;
(c) calculating the serine protease blood coagulation factor activation reaction time by correlation of the values measured in each of steps (a) and (b) with a value of required proportion of activated serine protease blood coagulation factor; and
(d) performing the serine protease blood coagulation factor activation reaction for the time calculated in step (c);
(e) terminating the reaction after the reaction time calculated in step (c).

In one embodiment of the invention, the correlation procedure described in step (c) is calculated in accordance with formula (I):

$$t = \frac{-\ln\left(\frac{akt0 \cdot (akt-1)}{akt \cdot (akt0-1)}\right)}{k(T) \cdot xb \cdot F0} \quad (I)$$

wherein "akt" refers to the required proportion of cleaved polypeptide, "akt0" refers to the initial proportion of cleaved polypeptide measured in step (b), "F0" refers to the initial concentration of the polypeptide (in g/l) measured in step (a), k(T) refers to the reaction constant for the given reaction (in L/g/min) as a function of temperature, T, and xb refers to the molar fraction. In one embodiment, k(T) is a polynomial or a spline which describes the variation of k with temperature. For rFVIIa, the following 3rd order polynomial was used: k(T)=k*(0.00001 T^3-0.00147 T^2+0.02566 T+0.86729) with T being the temperature (5-60° C.). In a similar fashion, pKa can be expressed as a function of temperature.

In one embodiment, the temperature is between 5° C. and 25° C., preferably 10° C. to 20° C.

In a further embodiment, the activation reaction is performed at room temperature (e.g. approximately 21.5° C.).

In the embodiment wherein the modification comprises cleavage of factor VII, the activation reaction is typically performed at a constant temperature.

Application of the invention to the activation of factor VII beneficially results in the production of fully activated factor VII molecules containing a minimum of degradation products.

The term "analogue" as used herein referring to a polypeptide means a modified peptide wherein one or more amino acid residues of the peptide have been substituted by other amino acid residues and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide. All amino acids for which the optical isomer is not stated are to be understood to mean the L-isomer.

Examples of factor VII analogues may be found in WO 02/22776, the analogues of which are herein incorporated by reference. In one embodiment, the factor VII analogue is selected from the group consisting of wt-FVIIa, K157A-FVIIa, V158T/M298Q-FVIIa, V158D/M298Q-FVIIa, V158D/M298K-FVIIa, V158D/E296V/M298Q-FVIIa, M298Q-FVIIa, V158D/E296V/M298Q/K337A-FVIIa, S336G-FVIIa, and K337A-FVIIa. In one embodiment, the factor VII analogue is a hyperactive analogue, i.e. one which has at least two fold greater amidolytic activity than wild-type factor VII. In a preferred embodiment, the factor VII analogue is V158D/E296V/M298Q-FVII(a) (Example 6 in WO 02/22776).

Measurement of the initial concentration of the polypeptide in step (a) may typically be performed by UV spectroscopy. In one embodiment, the concentration will be adjusted to between approximately 1.5 g/L and 2.2 g/L (e.g approximately 1.9 g/L).

Measurement of the initial proportion of cleaved polypeptide in step (b) may typically be performed by reduced SDS-PAGE, reduced or non-reduced HPLC or chip electrophoresis (e.g. Agilent Bioanalyzer). In one embodiment, step (b) is performed by chip electrophoresis (e.g. Agilent Bioanalyzer). In the embodiment wherein the polypeptide comprises factor VII, the initial proportion of activated factor VII(a) will typically be between 10 and 90% depending upon the purification conditions.

It will be appreciated that references to "required proportion of modified polypeptide" refer to any proportion of modification required by the user. In the embodiment wherein the modification comprises cleavage of factor VII, the required proportion of cleavage will be between 94 and 99%, such as between 95 and 97% (e.g. approximately 95%). These ranges would typically be selected to provide a high proportion of activation products (e.g. factor VII(a)) but minimise the amount of heavy chain degradation products (AA290 and AA315).

In the embodiment wherein the modification comprises cleavage of factor VII, the cleavage reaction additionally comprises the addition of an amine compound (e.g. histidine, Tris, lysine, arginine, phosphorylcholine, or betaine). In a further embodiment, the amine compound is histidine. In one embodiment, the amine compound is added to a final concentration of about 1 to 500 mM, such as about 10 to 100 mM (e.g. 10 mM).

In the embodiment wherein the modification comprises cleavage of factor VII, the cleavage reaction additionally comprises the addition of calcium ions (e.g. calcium chloride). In one embodiment, the calcium ions are added to a final concentration of about 1 to 50 mM, such as between 10 and 25 mM (e.g. 12 mM).

In the embodiment wherein the modification comprises cleavage of factor VII, the cleavage reaction additionally comprises the addition of sodium chloride. In one embodiment, the sodium chloride is added to a final concentration of about 1 to 100 mM, such as between 20 and 80 mM (e.g. 60 mM).

In one embodiment of the invention, the required proportion of serine protease cleavage is between 90 and 99%, such as between 94 and 99%, such as between 95 and 97%, such as between 96 and 98%, such as between 97 and 99%.

In the embodiment wherein the modification comprises cleavage of factor VII, the activation reaction is typically performed at a pH of between 6.0 and 8.0. The autocatalytic reaction of factor VII is pH dependent. As the pH is raised, the amidolytic activity of factor VII is initiated and therefore the reaction rate will increase accordingly. It is therefore desirable to choose a pH value between 6.0 and 8.0 and ensure that the reaction proceeds at this pH by appropriate buffering. If the pH varies during the activation reaction then the rate of activation will vary from that calculated in step (c) and therefore impact upon the quality of the resultant product.

Thus, in one embodiment, the method of the invention additionally comprises the step of selecting a pH of between 6.0 and 8.0 prior to initiation of the activation reaction and maintaining the reaction at the selected pH value during the activation reaction. In a further embodiment, the pH is selected from between 6.25 and 6.75 (e.g. 6.5±0.05).

In view of the substantial accuracy of the methodology described herein, it is desirable to ensure that the activation reaction is terminated immediately after the reaction time calculated in step (c). If the activation reaction is allowed to continue beyond the time calculated in step (c) then this will increase the potential presence of undesirable heavy chain degradation products. A number of alternative methods for termination are known to those skilled in the art, for example, the addition of silica to the reaction mixture. However, in one embodiment, the activation reaction is terminated by lowering the pH to a value below about 6.0, such as between 5.5 and 6.0 (e.g. 5.8). In one embodiment, the pH is lowered by the addition of a strong acid (e.g. 1M hydrochloric acid).

In a further embodiment of the invention, the correlation procedure described in step (c), used to calculate the reaction time (hereinafter referred to as "t") may be calculated in accordance with formula (II):

$$t = \frac{-\ln\left(\frac{akt0 \cdot (akt-1)}{akt \cdot (akt0-1)}\right)}{k \cdot xb \cdot F0} \tag{II}$$

wherein "akt" refers to the required proportion of cleaved polypeptide, "akt0" refers to the initial proportion of cleaved polypeptide measured in step (b), "F0" refers to the initial concentration of the polypeptide (in g/l) measured in step (a), k refers to the reaction constant for the given reaction (in L/g/min) and xb refers to the molar fraction.

The molar fraction (xb) can be calculated using the Henderson-Hasselbach relationship which correlates between the active fraction of the enzyme at any pH value. Typically, this relationship will be a non-linear correlation (e.g. sigmoidal).

In the embodiment wherein the modification comprises cleavage of factor VII, xb may be calculated based on the degree of protonisation of histidine. Serine proteases (including factor VII(a)) are characterised by a catalytic triad consisting of three residues: Serine 139, Histidine 57 and Aspartate 81. It is known that the histidine residue must be deprotonised in order to react and the serine protease is only active in a pH range above the pKa of histidine (which is 7.61).

Therefore, in the embodiment wherein the modification comprises cleavage of factor VII, xb may be calculated according to the following equation in formula (III):

$$xb = \frac{10^{pH-7.61}}{1 + 10^{pH-7.61}} \tag{III}$$

wherein pH refers to the selected pH of the reaction.

The value k may be calculated in accordance with the reaction kinetics of the given reaction intended to be measured. Thus, k is a physical constant which defines concentration dependency. Such a constant may generally be calculated in accordance with the sum of least squares which will be readily apparent to those skilled in the art. For example, in the embodiment wherein the polypeptide comprises factor VII, the value of k has been calculated as 0.29 L/g/min. Therefore, in the embodiment wherein the modification comprises cleavage of factor VII, the correlation procedure described in step (c) to calculate the reaction time ("t") may be calculated in accordance with formula (IV):

$$t = \frac{-\ln\left(\frac{akt0 \cdot (akt-1)}{akt \cdot (akt0-1)}\right)}{0.29 \cdot xb \cdot F0} \tag{IV}$$

Wherein akt, akt0, xb and F0 are as hereinbefore defined.

In a further embodiment of the invention, the correlation procedure described in step (c) is calculated by means of formula (V), in which xb of formula (II) is 1:

$$t = \frac{-\ln\left(\frac{akt0 \cdot (akt - 1)}{akt \cdot (akt0 - 1)}\right)}{k \cdot F0} \quad (V)$$

wherein "akt" refers to the required proportion of cleaved polypeptide, "akt0" refers to the initial proportion of cleaved polypeptide measured in step (b), "F0" refers to the initial concentration of the polypeptide (in g/l) measured in step (a) and k refers to the reaction constant for the given reaction (in L/g/min).

According to a third aspect of the invention there is provided a polypeptide obtainable according to the method as defined hereinbefore.

In different embodiments, said blood coagulation serine protease is Factor II or Factor VII or Factor IX or Factor X or Factor XI or Factor XII; or an analogue or derivative of any one of said blood coagulation factors.

In one embodiment, the polypeptide is a factor VII(a) or factor IX analogue or derivative.

The factor VII(a) or factor IX analogues or derivatives and pharmaceutical compositions comprising the factor VII (a) or factor IX analogues or derivatives according to the present invention may be used in the treatment of diseases alleviated by administration of human coagulation factor VII(a) or IX, such as a bleeding disorder e.g. hemophilia, a blood disease, hemarthrosis, hematomas, mucocutaneous bleeding, inherited blood disease, familial bleeding disorder, familial blood disease or factor replacement therapy. In one embodiment, the disease alleviated by administration of human coagulation factor VII(a) or IX is hemophilia, such as hemophilia B or Christmas disease.

Thus according to a further aspect of the invention there is provided a method of treating hemophilia which comprises administering to a patient a therapeutically effective amount of a factor VII(a) or IX analogue or derivative as defined hereinbefore.

There is also provided a factor VII(a) or a factor IX analogue or derivative, as defined hereinbefore, for use in the treatment of hemophilia.

There is also provided the use of a factor VII(a) or a factor IX analogue or derivative as defined hereinbefore in the manufacture of a medicament for the treatment of hemophilia.

There is also provided a pharmaceutical composition comprising a factor VII(a) or IX analogue or derivative as defined hereinbefore for use in the treatment of hemophilia.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active peptides to prevent the onset of the symptoms or complications. The patient to be treated is preferably a mammal, in particular a human being, but it may also include animals, such as dogs, cats, cows, sheep and pigs. It is to be understood, that therapeutic and prophylactic (preventive) regimes represent separate aspects of the present invention.

A "therapeutically effective amount" of a peptide as used herein means an amount sufficient to cure, alleviate or partially arrest the clinical manifestations of a given disease and its complications. An amount adequate to accomplish this is defined as "therapeutically effective amount". Effective amounts for each purpose will depend on the type and severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

According to a further aspect of the invention, there is provided a pharmaceutical formulation comprising a polypeptide as hereinbefore defined.

The formulation may further comprise a buffer system, preservative(s), tonicity agent(s), chelating agent(s), stabilizers and surfactants. In one embodiment of the invention the pharmaceutical formulation is an aqueous formulation, i.e. formulation comprising water. Such formulation is typically a solution or a suspension. In one embodiment of the invention the pharmaceutical formulation is an aqueous solution.

The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In one embodiment the pharmaceutical formulation is a freeze-dried formulation, whereto the physician or the patient adds solvents and/or diluents prior to use.

In one embodiment the pharmaceutical formulation is a dried formulation (e.g. freeze-dried or spray-dried) ready for use without any prior dissolution.

In one embodiment the invention relates to a pharmaceutical formulation comprising an aqueous solution of a peptide of the present invention, and a buffer, wherein said peptide is present in a concentration from 0.1-100 mg/ml, and wherein said formulation has a pH from about 2.0 to about 10.0.

In one embodiment of the invention the pH of the formulation is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

In one embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In one embodiment of the invention the formulation further comprises a pharmaceutically acceptable preservative. In one embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof.

In one embodiment of the invention the preservative is present in a concentration from 0.1 mg/ml to 20 mg/ml. In one embodiment of the invention the preservative is present in a concentration from 0.1 mg/ml to 5 mg/ml. In one embodiment of the invention the preservative is present in a concentration from 5 mg/ml to 10 mg/ml. In one embodiment of the invention the preservative is present in a concentration from 10 mg/ml to 20 mg/ml.

Each one of these specific preservatives constitutes an alternative embodiment of the invention. The use of a preservative in pharmaceutical compositions is well-known to the skilled person. For convenience reference is made to Remington: *The Science and Practice of Pharmacy*, 20$^{th}$ edition, 2000.

In one embodiment of the invention the formulation further comprises an isotonic agent. In one embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In one embodiment of the invention the isotonic agent is present in a concentration from 1 mg/ml to 50 mg/ml. In one embodiment of the invention the isotonic agent is present in a concentration from 1 mg/ml to 7 mg/ml. In one embodiment of the invention the isotonic agent is present in a concentration from 8 mg/ml to 24 mg/ml. In one embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 20$^{th}$ edition, 2000.

In one embodiment of the invention the formulation further comprises a chelating agent. In one embodiment of the invention the chelating agent is selected from salts of ethylenediaminetetraacetic acid (EDTA), citric acid, and aspartic acid, and mixtures thereof. In one embodiment of the invention the chelating agent is present in a concentration from 0.1 mg/ml to 5 mg/ml. In one embodiment of the invention the chelating agent is present in a concentration from 0.1 mg/ml to 2 mg/ml. In one embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: *The Science and Practice of Pharmacy*, 20$^{th}$ edition, 2000.

In one embodiment of the invention the formulation further comprises a stabilizer. The use of a stabilizer in pharmaceutical compositions is well-known to the skilled person. For convenience reference is made to Remington: *The Science and Practice of Pharmacy*, 20$^{th}$ edition, 2000.

More particularly, compositions of the invention are stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essex, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53).

Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L, D, or mixtures thereof) of a particular amino acid (e.g. glycine, methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In one embodiment of the invention the amino acids or amino acid analogues are used in a concentration, which is sufficient to prevent or delay aggregation of the protein.

In one embodiment of the invention methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L, D, or mixtures thereof) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In one embodiment of the invention the formulation further comprises a stabilizer selected from the group of high molecular weight polymers or low molecular compounds. In one embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a non-ionic surfactant, which protects the polypeptide against aggregation associated with freeze-thawing or mechanical shearing.

In one embodiment of the invention the formulation further comprises a surfactant. In one embodiment of the invention the surfactant is selected from a detergent, ethoxylated castor oil, polyglycolyzed glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives—(e.g. sodium tauro-dihydrofusidate etc.), long-chain fatty acids and salts thereof. C6-C12 (eg. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N_\alpha$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quaternary ammonium bases) (e.g. cetyl-trimethylammonium bromide, cetylpyridinium chloride), non-ionic surfactants (eg. Dodecyl β-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy*, 20$^{th}$ edition, 2000.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing a peptide of the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the peptide of the present invention, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of a peptide of the present invention, using, for example a metered dose inhaler, dry powder inhaler and a nebulizer, all being devices well known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres and nanoparticles.

Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the peptide of the present invention the form of a nasal or pulmonal spray. As a still further option, the pharmaceutical compositions containing the peptide of the present invention can also be adapted to transdermal administration, e.g. by needle-free injection or from a patch, optionally an iontophoretic patch, or transmucosal, e.g. buccal, administration.

The invention will now be described with reference to the following non-limited Examples:

Methodology

Calculation of Initial Proportion of Activation

The initial proportion of activation was determined using the Agilent Bioanalyser 2100, a chip based apparatus for conducting analytic electrophoresis, using an Agilent Protein 80 kit (Agilent 5067-1515). The Analysis was performed using the manufacturers instructions provided in "Agilent 2100 Bioanalyzer 2100 Expert User's Guide", Manual Part number: G2946-90000, Edition: November 2003 and "Agilent Protein 80 Kit Quick Start Guide", Part Number: G2938-90063, Edition April 2007 (both from: Agilent Technologies, Deutschland GmbH, Hewlett-Packard-Straße 8, 76337 Waldbronn, Germany).

In a 500 microlitre eppendorf tube, to 4 microlitres of sample was added 2 microlitres sample buffer from the protein 80 kit. The sample was boiled for five minutes in a heating block at 100° C. The sample was allowed to cool for 10 seconds before 15 seconds of centrifugation in a picofuge. 84 microlitres of purified water was added and the vial was mixed. The method analysis was run according to the above mentioned manufacturers instructions which are able to resolve: Heavy chain FVII(a), Light Chain FVII(a), and single chain FVII which elute in that respective order. The proportion of activation is the ratio between Heavy chain FVII(a) (HC)+Light Chain FVII(a) (LC) relative to the total FVII (HC+LC+SC). For example:

$$\text{Proportion of activation} = (HC+LC)/(HC+LC+SC)*100\%$$

EXAMPLES

Example 1

Calculation of Reaction Time for the Activation of Human Factor VII 6.316 kg of V158D/E296V/M298Q-FVII(a) (Example 6 in WO 02/22776) solution containing 10 mM histidine, 12 mM CaCl$_2$, 60 mM NaCl, pH 6.0 (at 5° C.) was measured by UV280 and had an absorbance of 2.31 AU, using a 1 cm lightpath. The concentration was calculated using the molar absorbance coefficient (0.7 g/kg*AU) to be 1.62 g/kg. The initial proportion of activation was determined to be 20% in accordance with the above mentioned protocol.

The variables for the reaction were decided to be as follows:
required proportion of activation: 95%;
pH: 6.50;
temperature: 21.5° C.

The activation time was calculated in accordance with the equation of formula (I) to be 128 minutes.

The activation reaction was started by adjusting pH upwards to 6.50 (at 21.5° C.) using 25 ml of 1M NaOH. After 128 mins, the pH was lowered again using 22 ml 1M HCl to 5.80 (22.3° C.). After ending the activation reaction, a sample was subjected to analysis, using the above mentioned methodology, which reported the proportion of activation to be 95.6%.

The actual proportion of activation varied from that predicted by the equation of formula (I) by only 0.6% following over 2 hours of enzymatic activation.

Example 2

Further Calculations of Reaction Time for the Activation of Human Factor VII

This experiment was performed on 5 separate purified batches of V158D/E296V/M298Q-FVII(a) (Example 6 in WO 02/22776) each having different values of initial proportion of activation to assess the consistency and accuracy of the method of the invention. This experiment was performed in an analogous manner to that described in Example 1 and the results can be seen in Table 1.

TABLE 1

| Variable | Batch 1 | Batch 2 | Batch 3 | Batch 4 | Batch 5 |
|---|---|---|---|---|---|
| Initial Proportion of Activation | 61 | 74 | 53 | 16 | 34 |
| Concentration (g/L) | 1.96 | 1.93 | 1.87 | 1.89 | 2.1 |
| Required Proportion of Activation | 92 | 96 | 94 | 96 | 98 |
| pH | 6.50 | 6.52 | 6.51 | 6.50 | 6.51 |
| Activation Time (min) | 51 | 52 | 71 | 126 | 108 |
| Actual final Proportion of activation | 90 | 96 | 96 | 96 | 98 |

The results from this assessment demonstrate that in 3 out of the 5 batches, the method of the invention predicted the final proportion of activation exactly. In the remaining 2 batches, the variation was only 2% which is not considered a significant or detrimental variation. Thus, table 1 shows cross validation of the model of the current invention. Experimental data is compared to the data that the model predicted in 5 different production batches in a pilot project. With highly variable input (16-74% active protease, "act time zero"), a constant output can be predicted and obtained.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The invention claimed is:

1. A method of obtaining a required proportion of activated factor VII, or an analogue or derivative thereof in a purified batch of factor VII/VIIa or an analogue or derivative thereof, which comprises the steps of:
   (a) measuring the initial concentration of the factor VII/VIIa, or analogue or derivative thereof;
   (b) measuring the initial proportion of activated factor VII, or analogue or derivative thereof;
   (c) calculating the activation reaction time of the factor VII, or analogue or derivative thereof, by correlation of the values measured in each of steps (a) and (b) with a value of required proportion of activated factor VII, or analogue or derivative thereof, the reaction time, t, being calculated in accordance with formula (I):

$$t = \frac{-\ln\left(\frac{akt0 \cdot (akt - 1)}{akt \cdot (akt0 - 1)}\right)}{k(T) \cdot xb \cdot F0} \quad (I)$$

wherein "akt" refers to the required proportion of activated factor VII, or analogue or derivative thereof, "akt0" refers to the initial proportion of activated factor VII, or analogue or derivative thereof, measured in step (b), "F0" refers to the initial concentration of the factor VII, or analogue or derivative thereof, (in g/l) measured in step (a), k(T) refers to the reaction constant for the given reaction (in L/g/min) as a function of temperature, T, and xb refers to the molar fraction, calculated according to the equation in formula (III), $$xb = \frac{10^{pH-7.61}}{1 + 10^{pH-7.61}} \quad (III)$$

wherein pH refers to the selected pH of the reaction;

(d) performing, at a pH of 6.0 to 8.0, the factor VII activation reaction, for the time calculated in step (c); and (e) terminating the reaction after the reaction time calculated in step (c), thereby obtaining the required proportion of the activated factor VII, or analogue or derivative thereof, wherein the terminating comprises lowering the pH to a value below about 6.0, wherein the activated factor VII, or analogue or derivative thereof, is wt-FVIIa, K157A-FVIIa, V158T/M298Q-FVIIa, V158D/M298Q-FVIIa, V158D/M298K-FVIIa, V158D/E296V/M298Q-FVIIa, M298Q-FVIIa, V158D/E296V/M298Q/K337A-FVIIa, S336G-FVIIa, or K337A-FVIIa.

2. The method according to claim 1, wherein k(T) is a polynomial or a spline.

3. The method according to claim 1, wherein the correlation procedure described in step (c) is calculated in accordance with formula (II):

$$t = \frac{-\ln\left(\frac{akt0 \cdot (akt-1)}{akt \cdot (akt0-1)}\right)}{k \cdot xb \cdot F0} \quad \text{(II)}$$

Wherein "akt", "akt0", "k", "xb", and "F0" are as defined in claim 1 and k is the reaction constant.

4. The method according to claim 3, wherein k=0.29.

5. A method of preventing degradation of an activated factor VII, or an activated factor VII analogue or derivative, in a purified batch of factor VII/VIIa or analogue or derivative thereof, to obtain a required proportion of activated factor VII, or an analogue or derivative thereof, said method comprising the steps of:

(a) measuring the initial concentration of the factor VII/VIIa, or analogue or derivative thereof;

(b) measuring the initial proportion of activated factor VII, or analogue or derivative thereof;

(c) calculating the activation reaction time of the factor VII, or analogue or derivative thereof, by correlation of the values measured in each of steps (a) and (b) with a value of required proportion of activated factor VII, or analogue or derivative thereof, the reaction time, t, being calculated in accordance with formula (I):

$$t = \frac{-\ln\left(\frac{akt0 \cdot (akt-1)}{akt \cdot (akt0-1)}\right)}{k(T) \cdot xb \cdot F0} \quad \text{(I)}$$

wherein "akt" refers to the required proportion of activated factor VII, or analogue or derivative thereof, "akt0" refers to the initial proportion of activated factor VII, or analogue or derivative thereof, measured in step (b), "F0" refers to the initial concentration of the factor VII, or analogue or derivative thereof, (in g/l) measured in step (a), k(T) refers to the reaction constant for the given reaction (in L/g/min) as a function of temperature, T, and xb refers to the molar fraction, calculated according to the equation in formula (III), $$xb = \frac{10^{pH-7.61}}{1 + 10^{pH-7.61}} \quad \text{(III)}$$

wherein pH refers to the selected pH of the reaction;

(d) performing, at a pH of 6.0 to 8.0, the factor VII activation reaction, for the time calculated in step (c); and (e) terminating the reaction after the reaction time calculated in step (c), thereby obtaining the required proportion of the activated factor VII, or analogue or derivative thereof, wherein the terminating comprises lowering the pH to a value below about 6.0, wherein the activated factor VII, or analogue or derivative thereof, is wt-FVIIa, K157A-FVIIa, V158T/M298Q-FVIIa, V158D/M298Q-FVIIa, V158D/M298K-FVIIa, V158D/E296V/M298Q-FVIIa, M298Q-FVIIa, V158D/E296V/M298Q/K337A-FVIIa, S336G-FVIIa, or K337A-FVIIa.

6. The method according to claim 1 wherein said factor VII, or analogue or derivative thereof, is V158D/E296V/M298Q-FVII(a).

7. The method according to claim 1 wherein the required proportion is between 94 and 99%.

8. The method according to claim 1 wherein the cleavage reaction additionally comprises the addition of calcium ions.

9. The method according to claim 1, wherein the activation reaction is performed at a pH of between 6.25 and 6.75.

10. The method according to claim 3, wherein xb=1.

11. The method according to claim 1 wherein step (d) is performed at a constant temperature.

12. The method according to claim 11, wherein the temperature is 5-60° C.

13. The method according to claim 9, wherein the activation reaction is performed at a pH of between 6.45 and 6.55.

* * * * *